United States Patent [19]

Noda et al.

[11] 4,400,520
[45] Aug. 23, 1983

[54] NOVEL PROCESS FOR PREPARING ISOINDOLINE DERIVATIVES

[75] Inventors: Kanji Noda, Chikushino; Akira Nakagawa; Toshiharu Motomura, both of Tosu; Hiroyuki Ide, Fukuoka, all of Japan

[73] Assignee: Hisamitsu Pharmaceutical Co., Inc., Tosu, Japan

[21] Appl. No.: 299,432

[22] Filed: Sep. 4, 1981

[30] Foreign Application Priority Data

Sep. 10, 1980 [JP] Japan .................................. 55-127526
Sep. 10, 1980 [JP] Japan .................................. 55-127529

[51] Int. Cl.$^3$ ............................................ C07D 209/46
[52] U.S. Cl. ................................ 548/472; 260/465 D; 560/35; 562/440
[58] Field of Search ............... 260/325 PH, 465 D; 562/440; 560/35; 548/472

[56] References Cited

U.S. PATENT DOCUMENTS 3,875,238  4/1975  Metlesics et al. ............ 260/325 PH
4,297,502  10/1981  Herrmann et al. ................... 560/35

OTHER PUBLICATIONS

G. Nannini et al., Arzneim.-Forsch. (Drug Res.) 23, Nr. 8 (1973) 1092–1100, New Analgesic-Anti-Inflammatory Drugs 1-Oxo-2-substituted Isoindoline derivatives.
Derwent Abstracts of: NL-7115288; Japanese Patent Gazette 53-37343; Jap. Pat. Appln. Laid-Open Gazette 51-6959; NL-7215830, Japanese Pat. Appln. Laid-Open Gazette 51-34147, 53-37655, 53-50157, 53-82772, 48-57965.

*Primary Examiner*—Donald G. Daus
*Assistant Examiner*—M. C. Eakin
*Attorney, Agent, or Firm*—Jordan and Hamburg

[57] ABSTRACT

A process for the preparation of an isoindoline derivative of the following general formula (II):

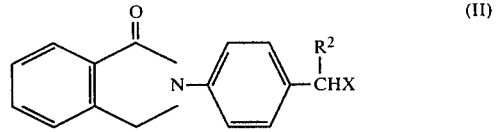

wherein $R^2$ is a hydrogen atom or lower alkyl group and X is a carboxyl group, carboalkoxy group, amide group or cyano group, which comprises
cycling a benzylidene derivative of the following general formula (I)

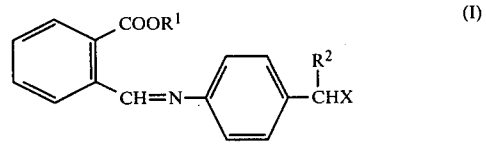

wherein $R^1$ is a hydrogen atom or lower alkyl group, and $R^2$ and X are as defined above, in the presence of a reducing agent such as sodium boron hydride. In one embodiment, the benzylidene derivative may be substituted by a reaction mixture containing the same, the reaction mixture being prepared by reacting o-phthalaldehydic acid or its ester with an aniline derivative.

3 Claims, No Drawings

NOVEL PROCESS FOR PREPARING ISOINDOLINE DERIVATIVES

This invention relates to a novel process for the preparation of an isoindoline derivative. More particularly, it relates to a novel process for preparing an isoindoline derivative represented by the following general formula (II)

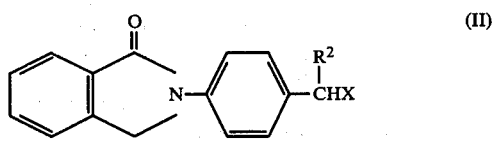

wherein $R^2$ is a hydrogen atom or lower alkyl group and X is a carboxyl group, carboalkoxy group, amide group or cyano group, which comprises
  cyclizing a benzylidene derivative represented by the following general formula (I)

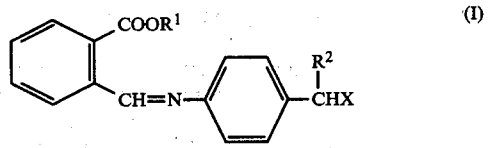

wherein $R^1$ is a hydrogen atom or lower alkyl group, and $R^2$ and X are as defined above, in the presence of a reducing agent such as sodium boron hydride or potassium boron hydride, or which comprises
reacting o-phthalaldehydic acid or its ester represented by the following general formula (III)

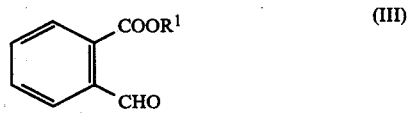

wherein $R^1$ is as defined above, with an aniline derivative represented by the following general formula (IV)

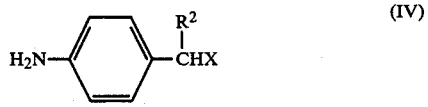

wherein $R^2$ and X are as defined above, to obtain a reaction mixture containing a benzylidene derivative represented by the following general formula (I)

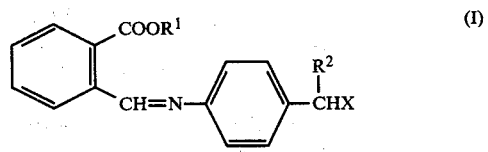

wherein $R^1$, $R^2$ and X are as defined above, and then
cyclizing the thus obtained reaction mixture without previous isolation of the benzylidene derivative of the formula (I), in the presence of a reducing agent such as sodium boron hydride or potassium boron hydride.

To explain $R^1$ and $R^2$ in the aforesaid general formulae (I) to (IV) more particularly, they are each a lower alkyl group such as methyl or ethyl group.

The compound, 1-oxo-2-{p-[(α-methyl)carboxymethyl]phenyl}-isoindoline (indoprofen) which is one of the compounds obtained by the process of this invention, has recently been known to exhibit very excellent activity as an anti-inflammatory or anodyne (or analgesic).

There have heretofore been known several methods for preparing indoprofen, and they may roughly be classified as follows.

Class 1. Methods comprising reacting an aniline derivative represented by the following general formula (V)

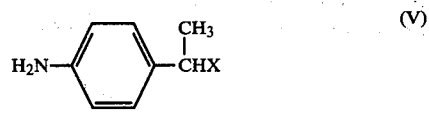

wherein X is a carboxyl, alkoxycarbonyl or cyano group, with o-cyanobenzylbromide, phthalide, thiophthalide or phthalaldehyde and then hydrolyzing the resulting reaction product with a base or mineral acid [Japanese Patent Gazette 51-11627, Arzneium-Forsch (Drug Res) 23, 1090 (1973)].

Class 2. Methods comprising reacting the aniline derivative of the aforesaid general formula (V) with phthalic anhydride or diethyl phthalate to obtain a compound having the following general formula (VI)

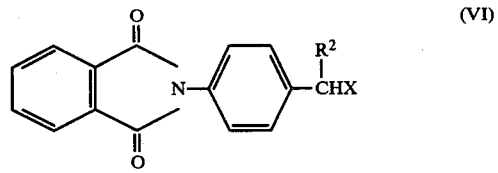

wherein $R^2$ and X are as defined above, reducing the thus obtained compound with a suitable reducing agent to obtain isoindoline and then, if desired, hydrolyzing it [Japanese Patent Gazette 51-11627, Arzeneium-Forsch (Drug Res) 23, 1090 (1973)].

Class 3. Methods comprising reacting the compound of the aforesaid general formula (V) with N-sulfonylphthalimide, N-alkoxycarbonylphthalimide or thiophthalic anhydride to obtain a compound having the following formula (VII)

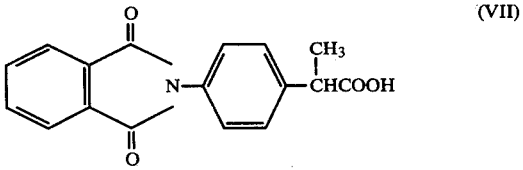

and then reducing the thus obtained compound with a suitable reducing agent (Japanese Patent Gazette No. 53-37343, Japanese Pat. Appln. Laid-Open Gazette No. 51-6959).

Class 4. Methods comprising reacting the compound of the aforesaid general formula (V) with benzaldehyde, reducing the resulting reaction product, reacting the thus reduced reaction product with phosgene to obtain a compound having the following general formula (VIII)

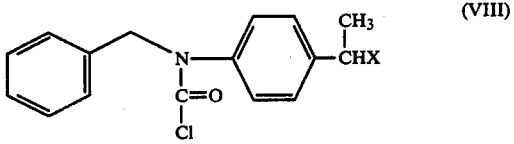

wherein X is as defined above, cyclizing the thus obtained compound (VIII) by the use of Friedel-Crafts' reaction and, if desired, hydrolyzing it (Japanese Pat. Appln. Laid-Open Gazette No. 48-57965).

Class 5. Methods comprising reacting the compound of the aforesaid general formula (V) with a compound of the following general formula (IX)

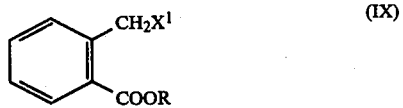

wherein R is a lower alkyl group and $X^1$ is a halogen atom (Japanese Pat. Appln. Laid-Open Gazette No. 51-34147).

Class 6. Methods comprising reducing under an acidic condition a compound of the following general formula (X) or (XI)

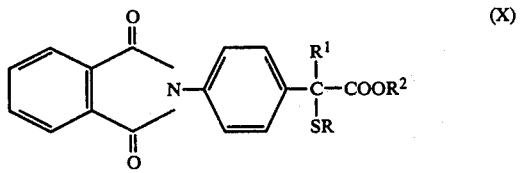

or

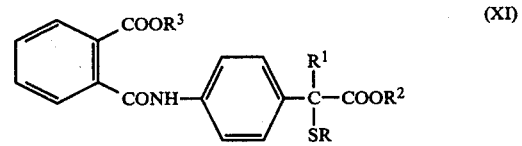

wherein R and $R^1$ are each a lower alkyl, and $R^2$ and $R^3$ are each a hydrogen atom or lower alkyl group (Japanese Pat. Appln. Laid-Open Gazette No. 53-82772).

Class 7. Methods for hydrolyzing a compound of the following formula (XII)

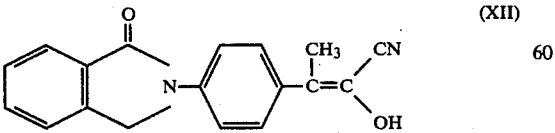

(Japanese Pat. Appln. Laid-Open Gazette No. 53-37655).

Class 8. Methods comprising oxidizing a compound of the following formula (XIII)

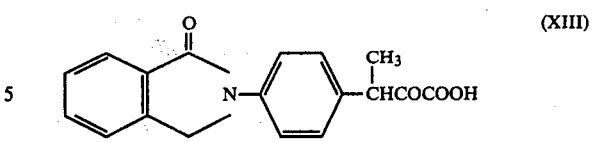

(Japanese Pat. Appln. Laid-Open Gazette No. 53-50157).

It cannot be said, however, that these known methods are an industrially satisfactory one. For example, in the methods of Class 1, there is raised a problem as to an economical and industrial production of the desired end compound since phthalaldehyde, thiophthalide or the like used as the starting material is expensive. The methods of Classes 2 and 3 are disadvantageous in that they have many steps since they comprise a reduction step and, if desired, a hydrolyzation step subsequent to the production of the dioxo compound, to obtain the desired end product. Methods of Class 4 are disadvantageous in that they use expensive platinum oxide in the reduction step, subsequently use phosgen which is strongly toxic and need many steps to obtain the desired end product. Methods of Class 5 raise a problem as to labor sanitation and manufacture since they need a halogenation agent (such as chlorine, bromine, N-bromosuccinic acid imide or N-chlorosuccinic acid imide) in the synthesis of an o-halomethylbenzoic acid ester which is the starting material therefor and in addition, they would not be an economical and industrially advantageous method since they use absolute ethanol, isopropanol or the like with is an expensive solvent. Methods of Classes (6), (7) and (8) raise an economical and industrial problem since they need many steps to obtain the desired end product, and, therefore, they would not be a fully satisfactory one.

On the other hand, the present inventors made intensive studies in an attempt to find an isoindoline derivative-producing process which eliminates the aforesaid disadvantages the conventional methods have, and, as the result of their studies, they found the following novel process. The novel process comprises the steps of:

reacting o-phthalaldehydic acid or an o-phthalaldehydic acid ester of the aforesaid formula (III) with an aniline derivative of the aforesaid formula (IV), the reaction proceeding in a short time when carried out in the presence of methanol, ethanol or diglyme (methanol being particularly preferred) at room temperature or somewhat elevated temperatures, thereby to obtain a reaction mixture mainly containing a benzylidene derivative of the aforesaid formula (I) in a high yield, and then reducing the thus obtained reaction mixture or the benzylidene derivative isolated therefrom with a reducing agent (such as sodium boron hydride or potassium boron hydride) in a molar ratio of preferably 1—2 at 0°-100° C., preferably 20°-40° C., for 1-24 hours thereby to the desired end product, an isoindoline derivative of the aforesaid formula (II) in a high yield.

As is seen from the above, the process of this invention may comprise reacting o-phthalaldehydic acid or an o-phthalaldehydic acid ester (III) with an aniline derivative (IV) in methanol or the like which is an inexpensive organic solvent, and then reducing the resulting reaction mixture (without isolating a benzylidene derivative (I) therefrom) with a reducing agent at room temperature or so in the same reaction vessel. Therefore, according to this invention, the desired end products may be obtained at a very low cost using simple reaction apparatuses and reaction operations. in addition, if desired, indoprofen may easily be obtained in a good yield by generally known hydrolysis of an isoindoline derivative containing ester, amide and cyano groups.

This invention will be better understood by the following Examples.

EXAMPLE 1

1.5 g of o-phthalaldehydic acid and 1.65 g of p-amino-(α-methyl)-phenylacetic acid were added to 30 ml of methanol to form a mixture which was agitated at room temperature for 30 minutes and then incorporated with 0.75 g of sodium boron hydride in several portions while cooling in an ice bath. The whole was reverted to room temperature, reacted for 3 hours and freed from the solvent by distillation under a reduced pressure to obtain a residue. The thus obtained residue was incorporated with 50 ml of water and then with a small amount of acetic acid to obtain an acidic solution, after which crystals precipitated from the solution were filtered off, dried and then recrystallized from ethanol thereby to obtain 2.6 g of 1-oxo-2'-{p-[(α-methyl)carboxymethyl]-phenyl}-isoindoline.

The thus obtained end product had the following melting point, infrared absorption spectrum, mass spectrum and elemental analysis:

Melting point: 214°14 215° C.

Infrared absorption spectrum: $\nu C=O$ (KBr) 1683 cm$^{-1}$

Mass spectrum: M+ 281.

Elemental analysis: $C_{17}H_{15}NO_3$: Theoretical C: 72.58, H: 5.37, N: 4.98. Found C: 72.53, H: 5.3, N: 4.92.

EXAMPLE 2

1.5 g of p-(o-carboxybenzylidene)-amino-(α-methyl)-phenylacetic acid was suspended in 30 ml of methanol and incorporated with 0.38 g of sodium boron hydride in several portions while ice cooling. The whole was reverted to room temperature, agitated for 3 hours and freed from the solvent by distillation under a reduced pressure to obtain a residue. The thus obtained residue was incorporated with 50 ml of water and then with a small amount of acetic acid to obtain an acidic solution, after which crystals precipitated from the thus obtained solution were filtered off, dried and recrystallized from ethanol to obtain 1.3 g of 1-oxo-2-{p-[(α-methyl)-carboxymethyl]-phenyl}-isoindoline.

The end compound so obtained had the following properties:

Melting point: 214°–215° C.

Infrared absorption spectrum: $\nu C=O$ (KBr) 1683 cm$^{-1}$.

Mass spectrum: M+ 281.

EXAMPLE 3

1.5 g of o-phthalaldehydic acid and 1.5 g of p-aminophenylacetic acid were added to 30 ml of methanol to form a mixture which was agitated at room temperature for one hour and incorporated with 0.54 g of potassium boron hydride in several portions. Then, the whole was reacted at room temperature of 5 hours and then freed from the solvent under a reduced pressure. The resulting residue was incorporated with 50 ml of water and then with a small amount of acetic acid to obtain an acidic solution, after which crystals precipitated from the thus obtained solution were filtered off, dried and recrystallized from ethanol to obtain 2.5 g of 1-oxo-2-{p-(carboxymethyl)-phenyl}-isoindoline.

The thus obtained end product had the following properties:

Melting point 210°–211° C.

Infrared absorption spectrum: $\nu C-O$ (KBr) 1685 cm$^{-1}$. Mass spectrum: M+ 267.

Elemental analysis: $C_{16}H_{13}NO_3$. Theoretical C: 71.90, H: 4.90, N: 5.24. Found C: 71.81, H: 4.98, N: 5.16.

EXAMPLE 4

1.5 g of o-phthalaldehydic acid and 1.3 g of p-aminobenzyl cyanide were added to 30 ml of methanol to form a mixture which was agitated at room temperature for 5 minutes and incorporated with 0.75 g of sodium boron hydried in several portions while cooling in a water bath. The whole was reverted to room temperature, reacted for 10 hours and freed from the solvent by distillation under a reduced pressure. The resulting residue was incorporated with 50 ml of water and then a small amount of acetic acid to obtain an acidic solution, after which crystals precipitated from said acidic solution were filtered off, dried and recrystallized from ethanol thereby to obtain 1.9 g of 1-oxo-2-{p-(carbonitrilemethyl)-phenyl}-isoindoline.

The thus obtained end compound has the following properties:

Melting point: 207°–208° C. Infrared absorption spectrum: $\nu C=O$ (KBr) 1685 cm$^{-1}$. Mass spectrum: M+ 248.

Elemental analysis: $C_{16}H_{12}N_2O$: Theoretical C: 77.40, H: 4.87, N: 11.28. Found C: 77.47, H: 4.73, N: 11.35.

EXAMPLE 5

1.5 g of o-phthalaldehydic acid and 1.9 g of p-amino-(α-methyl)-phenylacetic acid ethyl ester were added to 30 ml of methanol. The resulting mixture was agitated at room temperature for one hour and incorporated with 0.75 g of sodium boron hydride in several portions while cooling in an ice bath. The whole was reverted to room temperature, reacted for 7 hours and freed from the solvent by distillation under a reduced pressure. The resulting residue was incorporated with 50 ml of water and then with a small amount of acetic acid to obtain an acidic solution, after which the solution was subjected to extraction with ethyl acetate, dehydrated and freed from the solvent by distillation under a reduced pressure to obtain a residue. The residue so obtained was incorporated with isopropyl ether to crystallize out 2.6 g of 1-oxo-2-{p-[(α-methyl)-carboethoxymethyl]-phenyl}-isoindoline.

The thus obtained compound had the following properties:

Melting point: 101°–102° C.

Infrared absorption spectrum: $\nu C=O$ (KBr) 1725, 1677 cm$^{-1}$.

Mass spectrum: M+ 309.

Elemental analysis: $C_{19}H_{19}NO_3$: Theoretical C: 73.76, H: 6.19, N: 4.53 Found C: 73.71, H: 6.10, N: 4.61.

EXAMPLE 6

1.64 g of o-phthalaldehydic acid methyl ester and 1.65 g of p-amino-(α-methyl)-phenylacetic acid were added to 30 ml of methanol to form a mixture which was agitated at room temperature for one hour and incorporated with 0.75 g of sodium boron hydride in several portions while cooling in an ice bath. The whole was reverted to room temperature, reacted for 8 hours and then freed from the solvent by distillation under a reduced pressure. The resulting residue was incorporated with 50 ml of water and then with a small amount of acetic acid to obtain an acidic solution, after which crystals precipitated from this solution were filtered off, dried and recrystallized from ethanol thereby to obtain 2.5 g of 1-oxo-2-{p-[(α-methyl)-carboxymethyl]-phenyl}-isoindoline.

The compound so obtained had the following properties:

Melting point: 214°–215° C.

Infrared absorption spectrum: $\nu C=O$ (KBr) 1683 cm$^{-1}$.

Mass spectrum: M+ 281.

Elemental analysis: $C_{17}H_{15}NO_3$: Theoretical C: 72.58, H: 5.37, N: 4.98. Found C: 72.50, H: 5.32, N: 4.92.

EXAMPLE 7

1.64 g of o-phthalaldehydic acid methyl ester and 1.5 g of p-aminophenylacetic acid were added to 30 ml of methanol to form a mixture which was agitated at room temperature for one hour and incorporated with 0.54 g of potassium boron hydride in several portions. The whole was reacted at room temperature for 15 hours and freed from the solvent by distillation at a reduced pressure to obtain a residue. The thus obtained residue was incorporated with 50 ml of water and then with a small amount of acetic acid to form an acidic solution, after which crystals precipitated from said solution were filtered off, dried and recrystallized from ethanol thereby to obtain 2.4 g of 1-oxo-2-{p-(carboxymethyl)-phenyl}-isoindoline having the following properties:

Melting point: 210°–211° C.

Infrared absorption spectrum: $\nu C=O$ (KBr) 1685 cm$^{-1}$.

Mass spectrum: M+ 267.

Elemental analysis: $C_{16}H_{13}NO_3$: Theoretical C: 71.90, H: 4.90, N: 5.24. Found C: 71.84, H: 4.97, N: 5.18.

EXAMPLE 8

1.5 g of p-(o-methoxycarbonylbenzylidene)-aminophenylacetic acid was suspended in 30 ml of methanol and incorporated with 0.38 g of sodium boron hydride in several portions while ice cooling. The whole was then reverted to room temperature, agitated for 10 hours and freed from the solvent by distillation at a reduced pressure. The resulting residue was incorporated with 50 ml of water and then with a small amount of acetic acid to obtain an acidic solution, after which crystals precipitated from said solution were filtered off, dried and recrystallized from ethanol thereby to obtain 1.2 g of 1-oxo-2-{p-(carboxymethyl)-phenyl}-isoindoline.

The thus obtained compound had the following properties:

Melting point: 210°–211° C.

Infrared absorption spectrum: $\nu C=O$ (KBr) 1685 cm$^{-1}$.

Mass spectrum: M+ 267.

EXAMPLE 9

1.78 g of o-phthalaldehydic acid ethyl ester and 1.3 g of p-aminobenzyl cyanide were added to 30 ml of methanol to form a mixture which was agitated at room temperature for one hour and then incorporated with 0.75 g of sodium boron hydride in several portions while cooling in a water bath. The whole was reverted to room temperature, reacted for 10 hours and freed from the solvent by distillation at a reduced pressure to obtain a residue. The thus obtained residue was incorporated with 50 ml of water and then with a small amount of acetic acid to obtain an acidic solution, after which crystals precipitated from said solution were filtered off, dried and recrystallized from ethanol thereby to obtain 1.7 g of 1-oxo-2-{p-(carbonitrilemethyl)-phenyl}-isoindoline.

This compound had the following properties:

Melting point: 207°–208° C.

Infrared absorption spectrum: $\nu C=O$ (KBr) 1685 cm$^{-1}$,

Mass spectrum: M+ 248,

Elemental analysis: $C_{16}H_{12}N_2O$: Theoretical C: 77.40, H: 4:87, N: 11.28. Found C: 77:48, H: 4.79, N: 11.33.

EXAMPLE 10

1.64 g of o-phthalaldehydic acid methyl ester and 1.9 g of p-amino-(α-methyl)-phenylacetic acid ethyl ester were added to 30 ml of methanol to form a mixture which was agitated at room temperature for one hour and incorporated with 0.75 g of sodium boron hydride in several portions while cooling in an ice bath. The whole was reverted to room temperature, reacted for 7 hours and freed from the solvent by distillation at a reduced pressure to obtain a residue. The thus obtained residue was incorporated with 50 ml of water and then with a small amount of acetic acid to obtain an acidic solution which was extracted with ethyl acetate, dehydrated and freed from the solvent by distillation at a reduced pressure to obtain a residue. This residue was incorporated with isopropyl ether to be crystallized thereby to obtain 2.4 g of 1-oxo-2-{p-[(α-methyl)-carboethoxymethyl]-phenyl}-isoindoline.

This compound had the following properties:

Melting point: 101°–102° C.

Infrared absorption spectrum: $\nu C=O$ (KBr) 1725, 1677 cm$^{-1}$.

Mass spectrum: M+ 309.

Elemental analysis: $C_{19}H_{19}NO_3$: Theoretical C: 73.76, H: 6.19, N: 4.53. Found C: 73.70, H: 6.12, N: 4.61.

Furthermore, in accordance with the procedure of Examples 1–10, there were synthesized the following compounds:

1-oxo-2-{p-[(α-methyl)-carbonitrilemethyl]-phenyl}-isoindoline Melting point 196°–197° C., 1-oxo-2-{p-[(α-methyl)-carboamidomethyl]-phenyl}-isoindoline Melting point 248°–249° C., 1-oxo-2-{p-[(α-methyl)-carbomethoxymethyl]-phenyl}-isoindoline Melting point 128°–130° C., and 1-oxo-2-{p-[(α-ethyl)-carboxymethyl]-phenyl}-isoindoline Melting point 186°–188° C.

What is claimed is:

1. A process for preparing an isoindoline derivative represented by the following general formula (II)

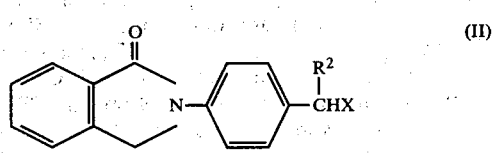

wherein $R^2$ is a hydrogen atom or lower alkyl group and X is a carboxyl group, carboalkoxy group, amide group or cyano group, which comprises cyclizing a benzylidene derivative represented by the following general formula (I)

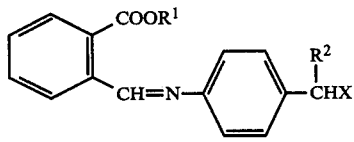
(I)

wherein $R^1$ is a hydrogen atom or lower alkyl group, and $R^2$ and X are as defined above, in the presence of a reducing agent.

2. A process for preparing an isoindoline derivative represented by the following general formula (II)

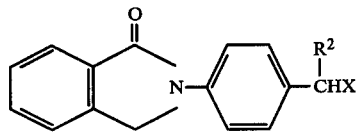
(II)

wherein $R^2$ is a hydrogen atom or lower alkyl group and X is a carboxyl group, carboalkoxy group, amide group or cyano group, which comprises reacting a member selected from the group consisting of o-phthalaldehydic acid and its ester represented by the following general formula (III)

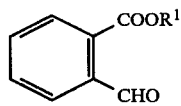
(III)

wherein $R^1$ is as defined above, with an aniline derivative represented by the following general formula (IV)

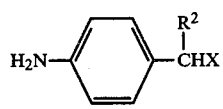
(IV)

wherein $R^2$ and X are as defined above, to obtain a reaction mixture containing a benzylidene derivative represented by the following general formula (I)

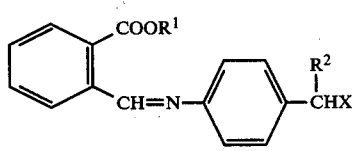
(I)

wherein $R^1$, $R^2$ and X are as defined above, and then cyclizing the thus obtained reaction mixture without previous isolation of the benzylidene derivative of the formula (I), in the presence of a reducing agent.

3. A process for preparing an isoindoline derivative according to claim 1 or 2, wherein the reducing agent is a member selected from the group consisting of sodium boron hydride and potassium boron hydride.

* * * * *